United States Patent [19]

Bowers et al.

[11] Patent Number: 4,832,851

[45] Date of Patent: May 23, 1989

[54] CENTRIFUGAL FORCE-ENHANCED FILTRATION OF FLUIDS

[75] Inventors: William F. Bowers, Topsfield; Douglas B. Tiffany, Danvers, both of Mass.

[73] Assignee: W. R. Grace & Co., Lexington, Mass.

[21] Appl. No.: 9,990

[22] Filed: Feb. 2, 1987

[51] Int. Cl.⁴ .................... B01D 13/00; B01D 33/00; B01D 35/02

[52] U.S. Cl. .................... 210/650; 210/321.67; 210/321.84; 210/360.1; 210/380.1; 210/455; 210/515; 210/518; 210/782; 422/101; 436/178; 494/16; 494/37; 494/48

[58] Field of Search .................... 494/16, 48, 37; 422/100, 101; 436/177, 178; 210/649, 650, 781, 782, 787, 359, 360.1, 361, 380.1, 433.2, 455, 472, 514, 515, 518, 321.67, 321.84

[56] References Cited

U.S. PATENT DOCUMENTS

| | | | |
|---|---|---|---|
| 1,386,340 | 8/1921 | Wuester | 210/359 |
| 3,481,477 | 12/1969 | Farr | 210/359 |
| 3,488,768 | 1/1970 | Rigopulos | 210/650 |
| 3,508,653 | 4/1970 | Coleman | 210/789 |
| 3,512,940 | 12/1968 | Shapiro | 422/101 |
| 3,661,265 | 5/1972 | Greenspan | 210/359 |
| 3,693,804 | 9/1972 | Grover | 210/359 |
| 3,761,408 | 9/1973 | Lee | 210/782 |
| 3,782,548 | 1/1974 | Bowen | 210/94 |
| 3,799,342 | 3/1974 | Greenspan | 210/359 X |
| 3,814,248 | 6/1974 | Lawhead | 210/789 |
| 3,814,258 | 6/1974 | Ayres | 210/359 |
| 3,832,141 | 8/1974 | Haldopoulos | 422/101 |
| 3,960,727 | 6/1976 | Hochstrasser | 210/782 |
| 4,035,150 | 7/1977 | Jaffe | 210/359 X |
| 4,483,825 | 11/1984 | Fatches | 422/101 X |
| 4,522,713 | 6/1985 | Nussbaumer et al. | 210/359 X |
| 4,632,761 | 12/1986 | Bowers et al. | 210/781 X |

FOREIGN PATENT DOCUMENTS 2133306B 11/1983 United Kingdom .

Primary Examiner—Ernest G. Therkorn
Assistant Examiner—W. Gary Jones
Attorney, Agent, or Firm—Bart G. Newland; William L. Baker

[57] ABSTRACT

A filtration apparatus and method is disclosed, the apparatus including a container tube for holding a sample to be filtered and a filtering vessel inserted therein. The filtering vessel carries a filter over its lower end and includes a chamber portion for receiving the filtrate. The method includes forcibly immersing the filtration vessel into the container tube, limiting the relative axial position therebetween, and subjecting the apparatus to centrifugation. The apparatus and method is useful for filtering dilute, concentrated and particle-laden samples.

27 Claims, 5 Drawing Sheets

CENTRIFUGAL FORCE-ENHANCED FILTRATION OF FLUIDS

BACKGROUND OF THE INVENTION

The present invention relates to methods and apparatus for filtering a fluid, and more particularly relates to the use of centrifugal force to aid such filtration.

It is well known that the filtration of fluids by microporous and ultraporous filters may be carried out under the influence of centrifugal force. For example, it is often desired to isolate proteins from liquid samples of bodily fluids or biological growth media in order either to concentrate the proteins or to produce a protein-free filtrate. U.S. Pat. No. 3,488,768 (P.N. Rigopulos, 1970) discloses several apparatus and methods for performing such filtration. Rigopulos also teaches that in addition to providing the trans-membrane force necessary to move the liquid through the filter, centrifugal force can be used to maintain the working surface of the filter free from a clogging build-up of protein or sediment.

U.S. Pat. No. 3,960,727 (Hochstrasser) discloses methods and apparatus for separating blood serum from clotted whole blood, preferably aided by centrifugal force. A sample to be filtered is contained in a first tube and a second tube, including a filter at its lower end, is placed therein. The second tube slowly sinks down into the first tube and through the sample, filtering the sample as it sinks. Sinking is advantageously accelerated by subjecting the assembly to centrifugal force by spinning the assembly in a centrifuge.

We have found that during the filtration of rather dilute solutions, such as dilute solutions of proteins or polypeptides, the "full floating" inner filtration tube design of Hochstrasser does not provide optimal trans-membrane pressure during centrifugation. Other problems occur in other devices during the filtration of highly concentrated solutions or solutions containing a large volume of particulate matter, as the filter may rapidly become clogged by the solute or particles. A need remains for apparatus and methods of performing centrifugal force-enhanced filtration of fluids.

An object of the present invention is to provide filtration methods and apparatus useful for both dilute solutions and particle-laden samples.

Another object of the present invention is to provide such an apparatus which, when placed within a 50 ml centrifuge tube carrier, is capable of filtering a 5 to 15 ml volume of sample.

A further object of this invention is to provide complete containment of biohazardous samples during centrifugal force-enhanced filtration.

The present invention satisfies these needs by providing methods and apparatus for filtering a fluid, including both relatively dilute solutions of e.g. protein(s) or polypeptide(s) and relatively particulate samples such as fermentation broth containing cells or whole blood. The apparatus consists of a container for holding a sample of liquid to be filtered, the container having an open end and a closed end. A filtering vessel is installed within the container and includes a chamber for receiving filtered fluid. The filtering vessel is preferably cylindrical and has an open upper end and an opening at its lower end which is covered by a filter, preferably an ultrafiltration (i.e. pore size of less than about 100 Angstroms) membrane carried by a filter support. High trans-membrane pressure and filtration rates are obtained by forcibly immersing the end of the filtering vessel which carries the filter into the sample to create a pressure head above the filter. By "forcibly immersing" we mean immersing against the natural buoyancy of the filtering vessel. The immersed position of the filtering vessel must be maintained, and this is accomplished in our preferred embodiment by the combination of an annular locking cap and the engagement of a ridge on the filtration vessel with the inner edge of the annular cap. Although the pressure differential created by forcible immersion alone may not be sufficient to accomplish filtration, this pressure differential is greatly increased when, according to the inventive method, the apparatus is subjected to centrifugal force. The centrifugal force greatly amplifies the pressure differential between the inside and outside of the filtration vessel to force the sample liquid through the filter and into the filtration vessel. The centrifugal force simultaneously prevents the working side of the filter from becoming clogged with sediment. Liquid within the filtration vessel is known as "filtrate" while that portion of the sample remaining outside the filtration vessel is known as "retentate".

DETAILS

Figure 1:
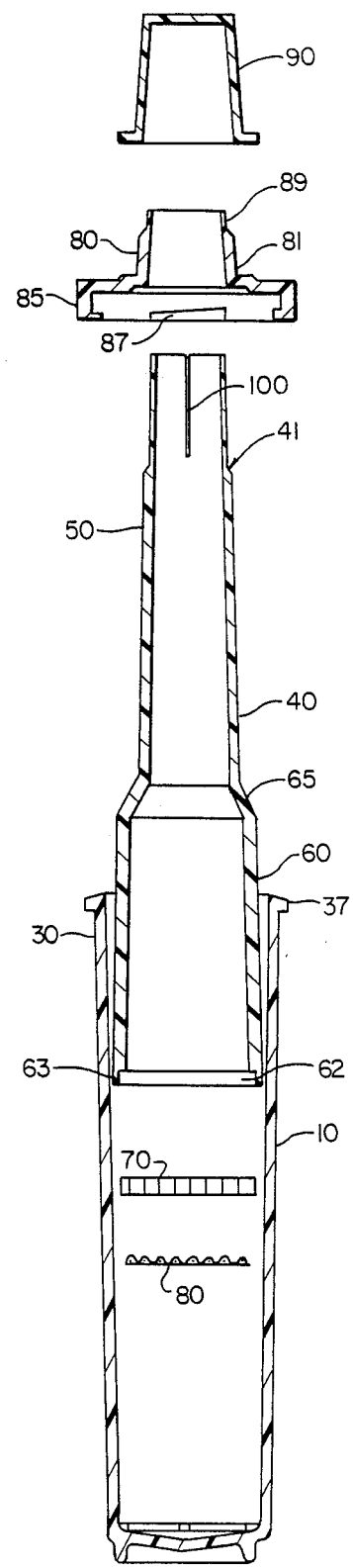
FIG. 1 is an exploded view of the present invention.

A preferred embodiment of the present filtration apparatus i illustrated in FIG. 1. The apparatus consists of a container 10 for holding a sample of fluid to be filtered, and in this preferred embodiment container 10 is an elongate tube having a sealed lower end 20 and an open upper end 30. A filtering vessel 40, which in this preferred embodiment also is an elongate tube, is adapted to fit inside of container 10. container 10 and filtering vessel 40 preferably are constructed of a synthetic plastic material which is inert to the fluids likely to be filtered in this apparatus, including bodily fluids and organic solvents. The apparatus preferably is dimensioned to fit within centrifuge rotors designed to accept standard 50 ml centrifuge tubes.

As seen in FIG. 1, the preferred filtering vessel 40 consists of a chamber portion 60 which had a diameter only slightly less than the diameter of the container 10. Chamber portion 60 is connected via a shoulder portion 65 to intermediate diameter to an elongate, narrow neck portion 50. The open lower end 62 of the filtering vessel 40 carries a filter which preferably includes a porous filter support 70 and a filter element 80. Filter element 80 may be of any desired pore size and is chosen with the size of the solute or particle to be filtered in mind. In the figures, filter element 80 is represented as a membrane filter in which case filter support 70 preferably consists of a molded plastic grid having channels and one or more ducts to pass permeate. Support 70 and filter 80 are secured to filtering vessel 40 by crimping lip 63 at the base of vessel 40 and bending the lip over the edge of the filter element and support. In the alternative, support 70 and filter 80 may be cemented to the base of vessel 40. Filter support 70 and filter element 80 may be replaced by other filtering materials, such as open cell foams, a wide variety of which are well known.

As seen in the Figures, this preferred embodiment of the present apparatus includes a first cap 80 which is adapted to maintain the filtering vessel 40 forcibly immersed within the sample in container 10 throughout the filtering process. First cap 80 has a base portion 85 which is adapted to engage the upper portion 30 of container 10, this engagement creating an airtight seal between first cap 80 and container 10. The base portion 85 carries a plurality of teeth 87 which engage corresponding teeth 37 on container 10 to provide a "bayonet"-type lock therebetween. A neck portion 89 of first cap 80 engages filtering vessel 40 via a friction fit between itself and the upper reduced-diameter portion of neck 50 of the filtering vessel, allowing filtrate to be decanted without leakage of retentate. The inner corner 84 of first cap 80 is of smaller diameter than filtering vessel 40 at ridge 41 to provide forcible immersion of the filtering vessel.

A second cap, designated by reference numeral 90, is responsible for sealing the contents of the filtering vessel 40 within the apparatus. As seen in the Figures, second cap 90 is adapted to fit tightly over the neck portion 81 of first cap 80 so that a friction fit is formed therebetween.

During filtration of the fluid sample, the sample passes from container 10, through filter 80 and filter support 70, and into the chamber portion 60 of filtering vessel 40. The air occupying the filtering vessel is displaced by the rising volume of filtrate and passes to chamber 10 via a thin capillary channel 100 formed in the outer surface of neck 50. Channel 100 is dimensioned to that the retentate will not pass therethrough during decantation.

Figure 2:
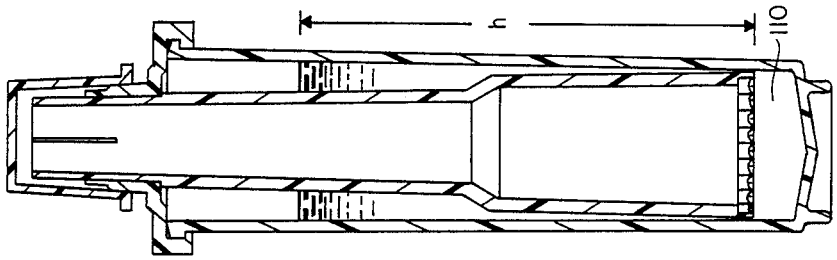
FIG. 2 is a view of the present invention prior to centrifugation.

FIG. 2 illustrates an assembled filtration apparatus which has been filled with about 15 ml of a fluid to be filtered. As seen, the shoulder and neck portions of filtering vessel 40 provide a reservoir for the fluid within the upper portion of container 10, although some of the sample occupies the space beneath filter 80 in a reservoir portion now present beneath the filtering vessel. Filtering vessel 40 has been forcibly immersed within into container 10 to create a pressure head (h) above filter 80. The device is now ready to be seated in a centrifuge rotor for centrifugation at a speed and g-force appropriate for the particular sample being filtered.

When centrifugation commences filtration vessel 40, under greatly increased buoyant fluid force from the sample, tries to rise within the container. Vessel 40 is maintained forcibly immersed, as ridge 41 on the neck of vessel 40 contacts the inner edge 84 of the cap 80 as seen FIG. 2. The filtration of particle-laden samples, such as fermentation broth, is facilitated as a reservoir 110 for particles is created below the filtration membrane. The membrane would rapidly become clogged by the large volume of filtered particles if the reservoir were not formed.

Figure 3B:
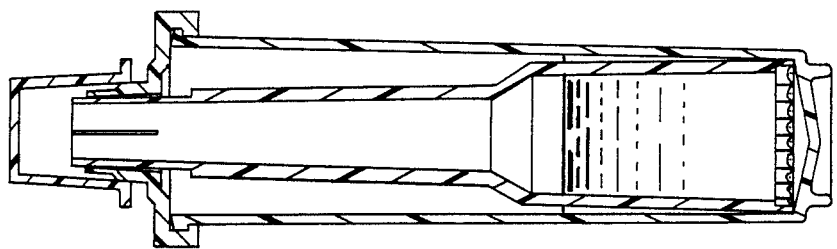
FIG. 3B is a view of the present invention following centrifugation and filtration of a dilute sample.
Figure 3A:
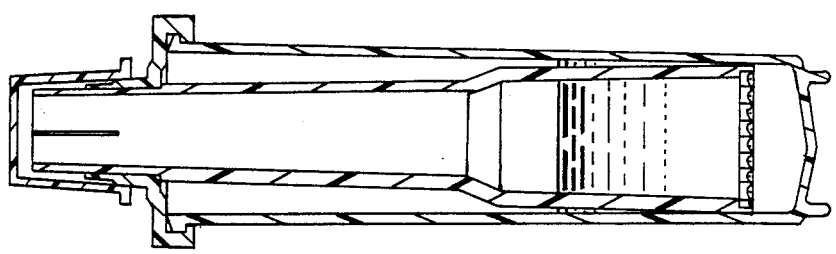
FIG. 3A is a view of the present invention following centrifugation and filtration of a highly concentrated or particle-laden sample.

FIG. 3A illustrates the present device following filtration of a particle-laden sample. Filtration vessel 40 containing the filtered liquid (filtrate) is resting on a bed of filtered particles contained within the reservoir 110 below the filter. The filtrate is easily decanted by removing second cap 90 and pouring out the liquid. The tight fit between first cap 80, the container 10 and filtering vessel 40 prevents the retentate from leaking during the quick decanting step. The combination of container 10 and first and second caps 80, 90 form an airtight barrier and thus none of the sample escapes as an aerosol.

FIG. 3b illustrates the present device following filtration of a much more dilute sample. Without a bed of particles to rest on, the filtration vessel 40 has sunk to the bottom of container 10 as the vessel has filled with filtrate. Approximately 3 to 3.5 of the original 15 ml of sample remains as retentate, thus providing about a five-fold concentration in the first spin. The filtrate may be decanted and the device reassembled for further centrifugation and filtration. A second filtration provides up to a 15 to 20-fold overall final concentration level.

EXAMPLES

The following examples illustrate the speedy and efficient filtration/concentration obtainable with the present invention when filtering a variety of samples:

Example 1

A Dilute Protein Solution

Figure 4:
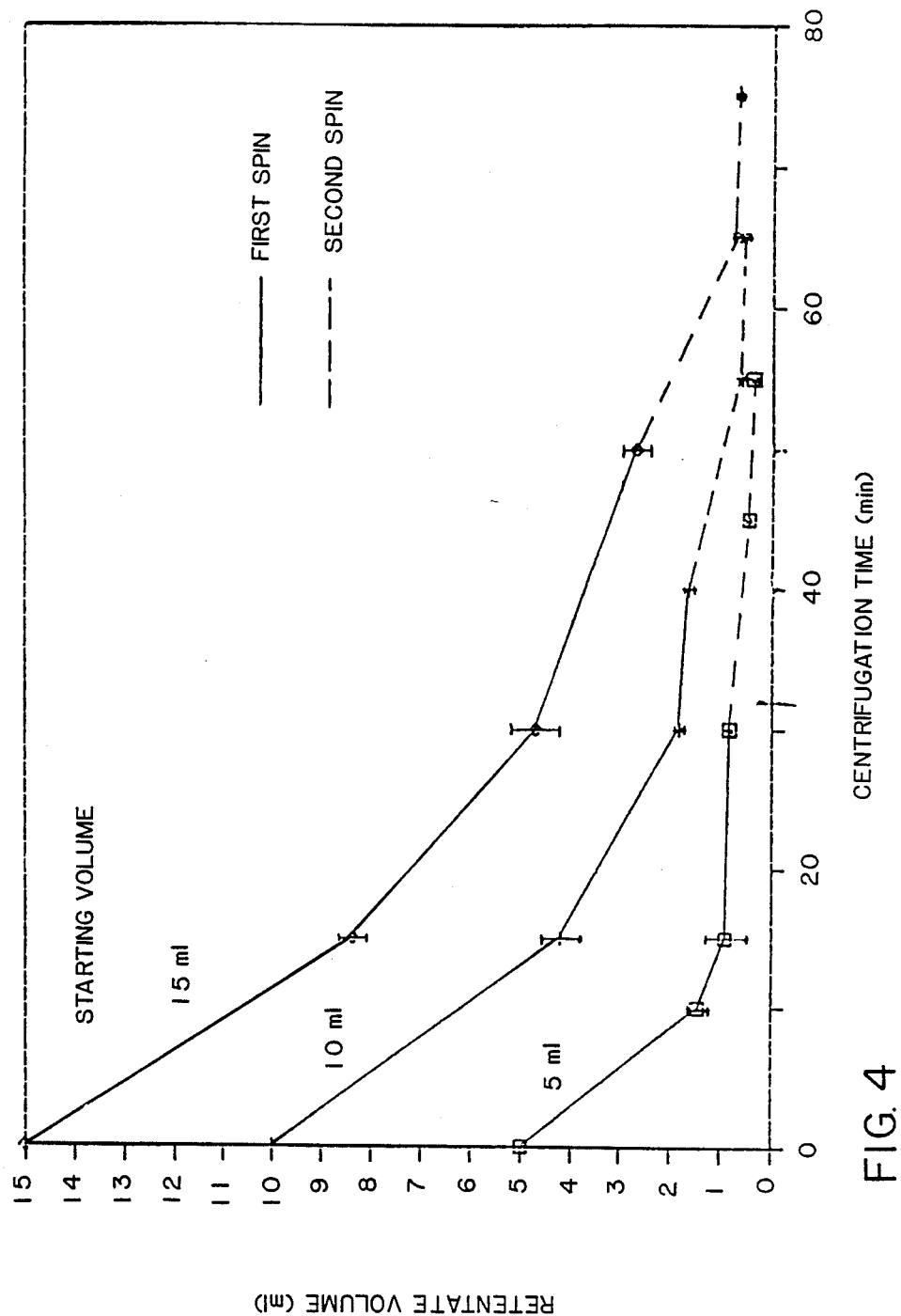
FIG. 4 is a plot of retentate volume vs. centrifugation time.

Four devices according to the present invention ("Centriprep TM 10", "10" signifying the 10,000 MW cut-off of the device's filtration membrane) were loaded with 5, 10 or 15 ml of a 1 mg/ml solution of bovine serum albumin and spun in a horizontal or fixed angle (45°) rotor for various lengths of time at 3000×g. After each spin the retentate volumes were determined by direct weight. Each data point up to the first equilibrium (FIG. 4, first spin) was generated with fresh devices. When the first equilibrium was reached, the filtrate was decanted, and the units were reassembled and respun for varying lengths of time. Since the curves for both rotors were very similar, the values for each point were averaged and plotted as one curve per starting volume (FIG. 4).

The data show that a dilute protein solution may be concentrated 20 fold in 55 to 75 minutes depending on the starting volume. During the first spin, approximately a five fold concentration can be achieved before the fluid levels inside and outside the filtering vessel come to equilibrium and filtration stops. After decanting filtrate, the device is spun again until the inner and outer fluid levels reach equilibrium, and a final 20 fold concentration factor is achieved. The final volume of the retentate is 0.5 to 0.7 ml.

The data below show the centrifugation times at 3000×g needed to achieve a certain concentration factor for both Centriprep and Amicon's other centrifugal concentrator, Centricon ®. Centricon ® is described in U.S. Pat. No. 4,632,761 which is incorporated by reference herein.

| Device | Initial Volume | Concentration Factor | Time (min) | Flux (ml/min) | Unit Flux (ml/min/cm$^2$) |
|---|---|---|---|---|---|
| Centriprep 10 | 15 | 5 | 45 | .273 | .096 |
| Centricon 10 | 2 | 5 | 45 | .036 | .039 |
| Centriprep 10 | 15 | 10 | 54 | .233 | .082 |
| Centricon 10 | 2 | 10 | 93 | .019 | .021 |

| Device | Initial Volume | Concentration Factor | Time (min) | Flux (ml/min) | Unit Flux (ml/min/cm²) |
| --- | --- | --- | --- | --- | --- |
| Centriprep 10 | 15 | 20 | 63 | .222 | .078 |
| Centricon 10 | 2 | 20 | 107 | .017 | .019 |

Centriprep 10 provides a twenty fold concentration starting with 15 ml, in less than seventy-five minutes. The overall flux was 0.222 ml/min, with a unit flux of 0.078 ml/min/cm² for this 2.84 cm² membrane area device. In the conventional Centricon, a twenty fold concentration beginning with 2 ml tool 110 minutes. Here, the overall flux was 0.017 ml/min, and the unit flux was 0.019 ml/min/cm². Centriprep 10, with three times the membrane surface area of Centricon provides thirteen times the absolute flux and four times the normalized flux during a twenty fold concentration of dilute protein.

Example II

A Concentrated Protein Solution

Figure 5:
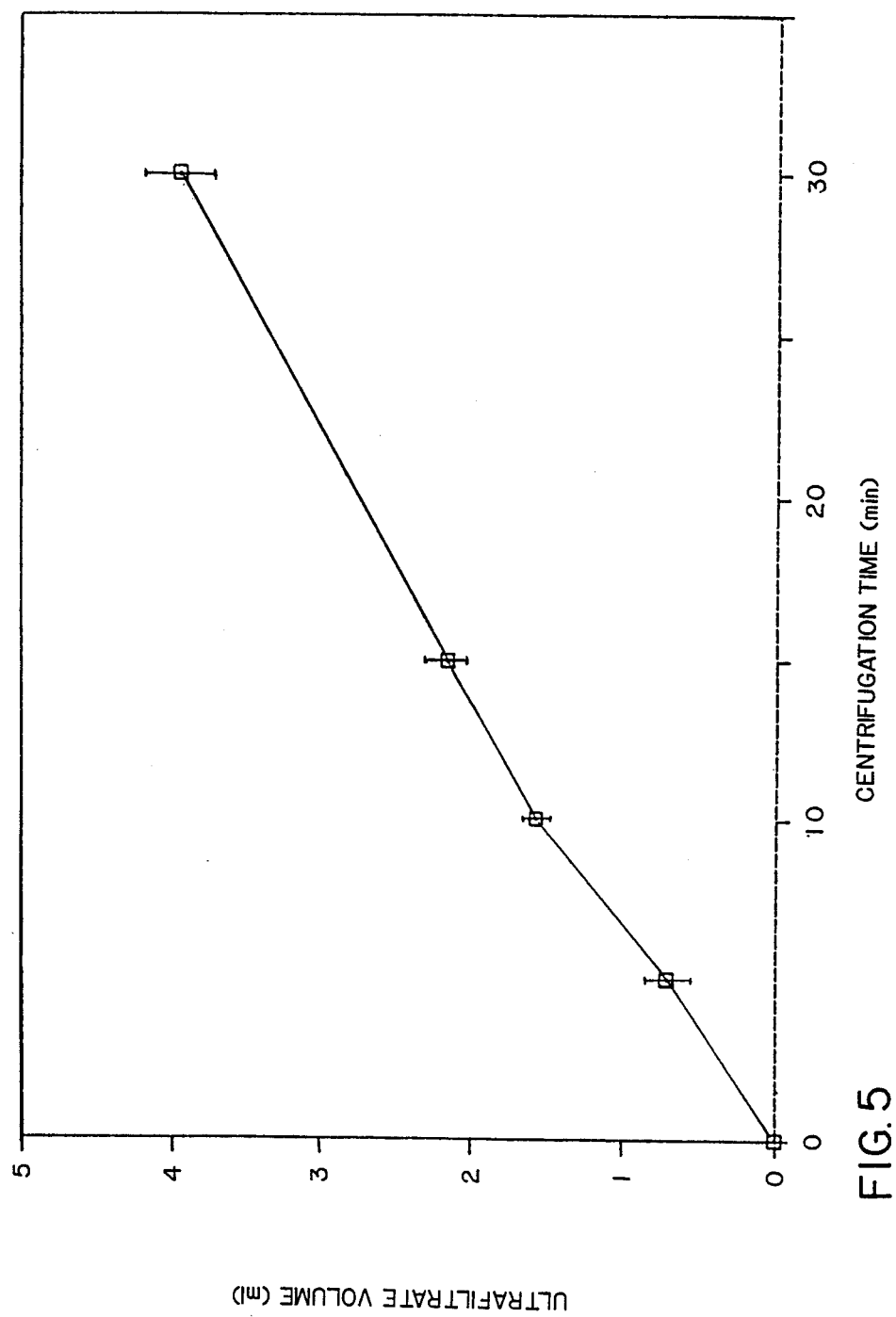
FIG. 5 is a plot of ultrafiltrate volume vs. centrifugation time.

Four Centriprep 30 devices (i.e., devices according to the present invention having a 30,000 MW cut-off membrane filter) were loaded with 15 ml of whole bovine serum and centrifuged for various lengths of time in a horizontal or fixed angle rotor at 3000×g. After each spin the ultrafiltrate was decanted and weighed. The data for both rotors were again averaged because of the good agreement, and plotted as one curve (FIG. 5).

The data demonstrate that even with concentrated, viscous protein solutions (approximately 80 mg/ml) several ml of protein free filtrate can be produced in a single 20 to 30 minute spin. Filtration rates are high becuase the filtrate vessel is allowed to float above the dense polarizing layer of protein in the bottom of the container tube.

When compared with Centrifree ™ (Amicon's centrifugal device designed to produce protein free filtrate from serum), Centriprep had over twice the unit flux (ml/min/cm²) at any given concentration factor.

Example III

A Particulate-Containing Solution

Figure 6:
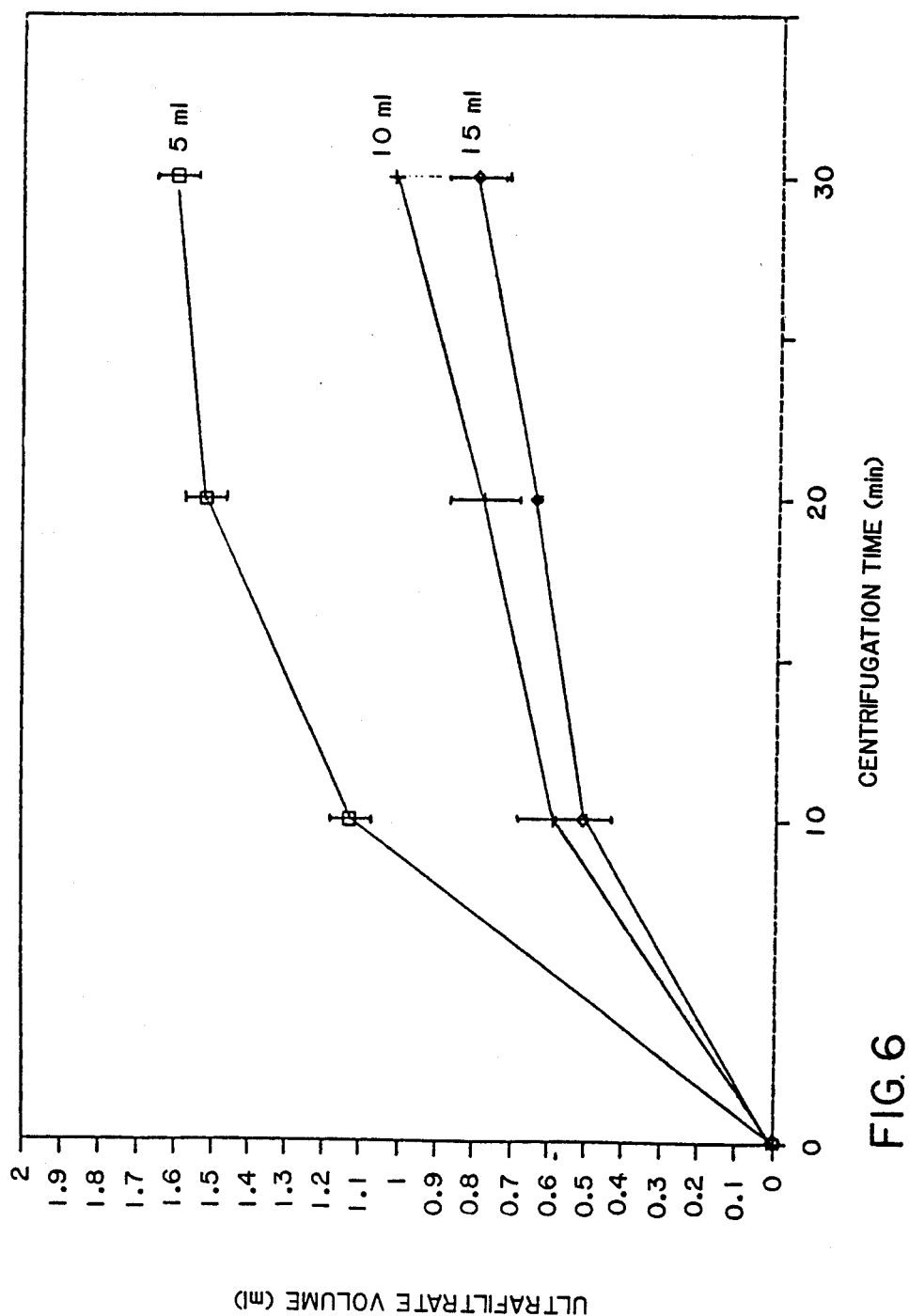
FIG. 6 is a plot of ultrafiltrate volume vs. centrifugation time.

Four Centriprep 10 devices were spun with 5, 10 and 15 ml of lysed yeast (15% wt/vol) for different lengths of time at 3000×g in a horizontal rotor. Cell free filtrates were weighed after each spin and the data plotted in FIG. 6.

By limiting the starting volume to 5 ml, and thereby minimizing the volume of particulates that can pack around and blind the membrane, the filtration rate can be sustained to yield a cell free filtrate volume of greater than 1.0 ml in a single 20 minute spin. Once again the filtration rate is optimized because the filtrate vessel is allowed to float above the packed layer of cells at the bottom of the container tube.

By contrast, with Centricon 10, only 0.12 ml of filtrate can be obtained from 2 ml of 15% yeast in 20 minutes. Increasing the spin time does not significantly increase the filtrate volume (0.185 ml after 60 minutes) because the Centricon, flow is greatly reduced due to the layer of cells packed directly on the membrane surface.

Example IV

Protein Recovery After Sample Concentration In Centriprep

Centriprep 30 and Centriprep 10 were loaded with 15 ml of 1 mg/ml bovine serum albumin and 15 ml of 0.25 mg/ml cytochrome C respectively. All devices were spun to their first equilibrium point and the filtrate was decanted. Devices were then spun to their second equilibrium point and the final filtrate was decanted and combined with the first. Filtrates, concentrates and starting material were weighed and assayed for protein, and percent recoveries were calculated. The following data demonstrate the excellent yield of samples concentrated in Centriprep.

| Device | Recovery from Filtrate | Recovery from Retentate | n |
| --- | --- | --- | --- |
| Centriprep 30 | 2.9 ± 2.1 | 93.6 ± 2.8 | 20 |
| Centriprep 10 | 2.3 ± 2.8 | 95.8 ± 3.7 | 40 |

We claim:

1. A method of filtering a composition comprising:
   placing a composition to be filtered into a container means;
   forcibly immersing a filtering vessel means for receiving filtrate into said composition in said container means, said filtering vessel means including an end having a filter means therein;
   limiting the axial position of the filtering vessel means relative to the container means by placing a means into engagement between the filtering vessel means and the container means to provide limited movement there maintaining said filtering vessel means forcibly immersed; and
   subjecting said container means, filtering vessel means and composit9ion to centrifugal force and thereby effecting filtration.

2. A method of claim 1 wherein during said subjecting step said filtering vessel means fills with filtrate and sinks within said composition.

3. A method of claim 1 wherein said container means and filtering vessel means each comprise an elongate cylinder, the filtering vessel means having a diameter less than the diameter of the container means.

4. A method of claim 3 wherein said filtering vessel means comprises a chamber portion having said filter means therein, a neck portion having a diameter less than the diameter of the chamber portion, and a shoulder portion connecting said neck and chamber portions.

5. A method of claim 4 wherein said neck portion comprises capillary means for allowing air to flow between said filtering vessel means and said container means.

6. A method of claim 4 wherein said limiting step comprises placing a cap means over adjacent upper ends of said container means and the neck portion of said filtering vessel means.

7. A method of claim 6 wherein said cap means includes tooth means for engaging corresponding tooth means on the upper end of said container means.

8. A method of claim 7 wherein said cap means comprises a first member and a second member, said first member adapted to effect a seal with the upper portion of the container means and including a channel adapted to receive the neck portion of the filtering vessel means, said second member adapted to effect a seal with said first member.

9. A method of claim 8 further comprising removing said second member and decanting a filtrate from said filtering vessel.

10. A method of claim 1 wherein said limiting step comprises placing a cap means into engagement between said container means and said filtering vessel means.

11. A method of claim 1 wherein said filter means comprises a membrane filter and said filter vessel means comprises attachment means for attaching said filter means thereto.

12. A method of claim 1 wherein said attachment means comprises a lip of said filtering vessel.

13. A method of claim 1 further comprising decanting a filtrate from said filtering vessel.

14. A filtration apparatus, comprising:
   a container means for containing a sample to be filtered and comprising an elongate tube having an upper open end and a lower closed end;
   a filtering vessel means for receiving filtrate and comprising an elongate tube adapted to be inserted into said container means, said filtering vessel means having an upper open end and a lower end covered by a filter means; and
   cap means for sealing said sample in said apparatus, said cap means comprising means for engagement between said filtering vessel means and said container means limiting the axial position of said filtering vessel means relative to said container means.

15. An apparatus of claim 14 wherein said filtering vessel means comprises a chamber portion having a diameter, a neck portion having a diameter less than the diameter of the chamber portion, and a shoulder portion connecting the chamber portion and the neck portion and having a diameter intermediate therebetween.

16. An apparatus of claim 15 wherein said filter means comprises a porous filter support and a filtration membrane, said filter support and membrane being secured to said filtering vessel means by an attachment means.

17. An apparatus of claim 16 wherein said attachment means comprises a lip portion of said filtering vessel means.

18. An apparatus of claim 16 wherein said filtration membrane comprises an ultrafiltration membrane.

19. An apparatus of claim 15 wherein said filter means comprises a membrane secured to said filtering vessel means by a crimped lower lip of said filtering vessel means.

20. An apparatus of claim 15 wherein said means limiting the position of said filtering vessel means comprises an inner edge portion of said cap means adapted to engage the neck portion of said filtering vessel means.

21. An apparatus of claim 20 wherein said neck portion of said filtering vessel means comprises a ridge portion adapted to engage the inner edge portion of said cap means.

22. An apparatus of claim 15 wherein the neck portion of said filtering vessel means comprises a capillary channel to allow equilibrium of pressure within said filtering vessel means and said container means.

23. An apparatus of claim 14 wherein said cap means includes a tooth means for securing said cap means to said container means by engaging a corresponding tooth means on said container means.

24. An apparatus of claim 14 wherein said cap means comprises a first member adapted to effect a seal with the upper open end of said container means and including a channel adapted to receive a neck portion of said filtering vessel means, and a second member adapted to engage said first member while sealing the open upper end of said filtering vessel means.

25. An apparatus of claim 24 wherein said first member comprises tooth means for engaging corresponding tooth means disposed on the upper portion of said container means.

26. A method of filtering a composition comprising:
   placing a composition to be filtered into a container means;
   forcibly immersing a filtering vessel means for receiving filtrate into said composition in said container means, said filtering vessel means including an end having a filter means therein;
   limiting the axial position of the filtering vessel means relative to the container means by placing a means into engagement between the filtering vessel means and the container means to prevent free from the filtering vessel means; and
   subjecting said container means, filtering vessel means and composition to centrifugal force and thereby effecting filtration.

27. A method of filtering a composition comprising, in the following sequence;
   placing a composition to be filtered into a container means;
   forcibly immersing a filtering vessel means for receiving filtrate into said composition in said container means, said filtering vessel means including an end having a filter means therein;
   limiting the axial position of the filtering vessel means relative to the container means by placing a means into engagement between the filtering vessel means and the container means to maintain said vessel means forcibly immersed; and
   subjecting said container means, filtering vessel means and composition to centrifugal force and thereby effecting filtration.

* * * * *